United States Patent [19]

Tschernezky

[11] 4,407,279
[45] Oct. 4, 1983

[54] APPARATUS FOR INHALATION

[76] Inventor: Wladimir Tschernezky, 15 Belgrave Lodge, 36 Wellesley Rd., London, W.4, England

[21] Appl. No.: 296,954

[22] Filed: Aug. 27, 1981

[30] Foreign Application Priority Data

Aug. 29, 1980 [GB] United Kingdom ............... 8027934

[51] Int. Cl.³ .......................................... A61M 15/00
[52] U.S. Cl. ......................... 128/200.11; 128/203.22; 128/203.26
[58] Field of Search ...................... 128/200.11, 200.12, 128/200.13, 203.12, 203.22, 203.26, 203.28, 203.29, 204.13, 254, 256, 257

[56] References Cited

U.S. PATENT DOCUMENTS

| 47,434 | 4/1865 | Lighthill | 128/200.11 |
| 374,402 | 12/1887 | Fell | 128/203.28 |
| 2,076,461 | 4/1937 | Hipsley | 128/203.26 |
| 2,166,574 | 7/1939 | Adolphsen | 128/200.13 |

FOREIGN PATENT DOCUMENTS

| 476110 | 7/1915 | France | 128/200.11 |
| 1004803 | 4/1952 | France | 128/203.26 |
| 130788 | 3/1929 | Switzerland | 128/256 |
| 30 | of 1869 | United Kingdom | 128/200.11 |

Primary Examiner—Henry J. Recla
Attorney, Agent, or Firm—Fleit, Jacobson, Cohn & Price

[57] ABSTRACT

Apparatus for inhalation comprising a single vacuum flask for holding a liquid and from which liquid vapor is to be inhaled, closure means for closing one end of the flask after the liquid has been introduced, air supply means, a connecting tube which passes through the closure means and via which air for inhalation is arranged to be fed from the air supply means to a region inside the flask adjacent the end remote from the closure means so as to bubble up through the liquid when contained therein, inhalation tube means which passes through the closure means for collecting the air after it has bubbled up through the liquid and which is adapted at one end thereof remote from the flask to fit to the nostrils whereby direct inhalation of air and vapor into the nostrils is facilitated, a thermometer which passes through the closure means and which is for measuring the temperature of the liquid in the flask, and a measuring cup which is for measuring the amount of liquid to be provided in the flask and which screws over the bottom of the flask.

9 Claims, 4 Drawing Figures

APPARATUS FOR INHALATION

This invention relates to apparatus for inhalation. Inhalation is a widely applied method of treating diseases of the nose, throat and also the trachea and bronchs. For this purpose inhalation of wet steam or vapour arising from a dish containing hot water or from a special inhaler is known. However all known inhalers have the disadvantage that beneficial vapours are not directed directly into the nostrils.

According to the present invention apparatus for inhalation comprises a single vacuum flask for holding a liquid and from which liquid vapour is to be inhaled, closure means for closing one end of the flask after the liquid has been introduced, air supply means, a connecting tube which passes through the closure means and via which air for inhalation is arranged to be fed from the air supply means to a region inside the flask adjacent the end remote from the closure means so as to bubble up through the liquid when contained therein, inhalation tube means which passes through the closure means for collecting the air after it has bubbled up through the liquid and which is adapted at one end thereof remote from the flask to fit to the nostrils whereby direct inhalation of air and vapour into the nostrils is facilitated, a thermometer which passes through the closure means and which is for measuring the temperature of the liquid in the flask, and a measuring cup which is for measuring the amount of liquid to be provided in the flask and which screws over the bottom of the flask.

The air supply means may comprise pump means. The pump means may be a manually operated pump or it may be an electrical pump. The air supply means may also be a cylinder of compressed air with appropriate air supply tubes.

The inhalation tube means may comprise two tubes and the end of each of the two tubes remote from the closure means may be fitted with an injector piece anatomically designed to fit the nostrils.

The connecting tube may include a length of rigid pipe which projects above the closure means and passes through the closure means and extends into the container.

When the pump means is sufficiently powerful, the end of the connecting tube may be terminated with an air stone gas bubble producer.

When the closure means is a push in closure means, the apparatus may advantageously include a safety cover for constraining the push in closure means in the event that the container should be over pressurised during use to the extent that the closure means is caused to blow out of the container.

When the closure means is a screw closure means, the apparatus may advantageously include a pressure release valve for releasing pressure from within the container in the event that the container should be over pressurised during use.

Embodiments of the invention will now be described solely by way of example and with reference to the accompanying drawings in which.

Figure 1:
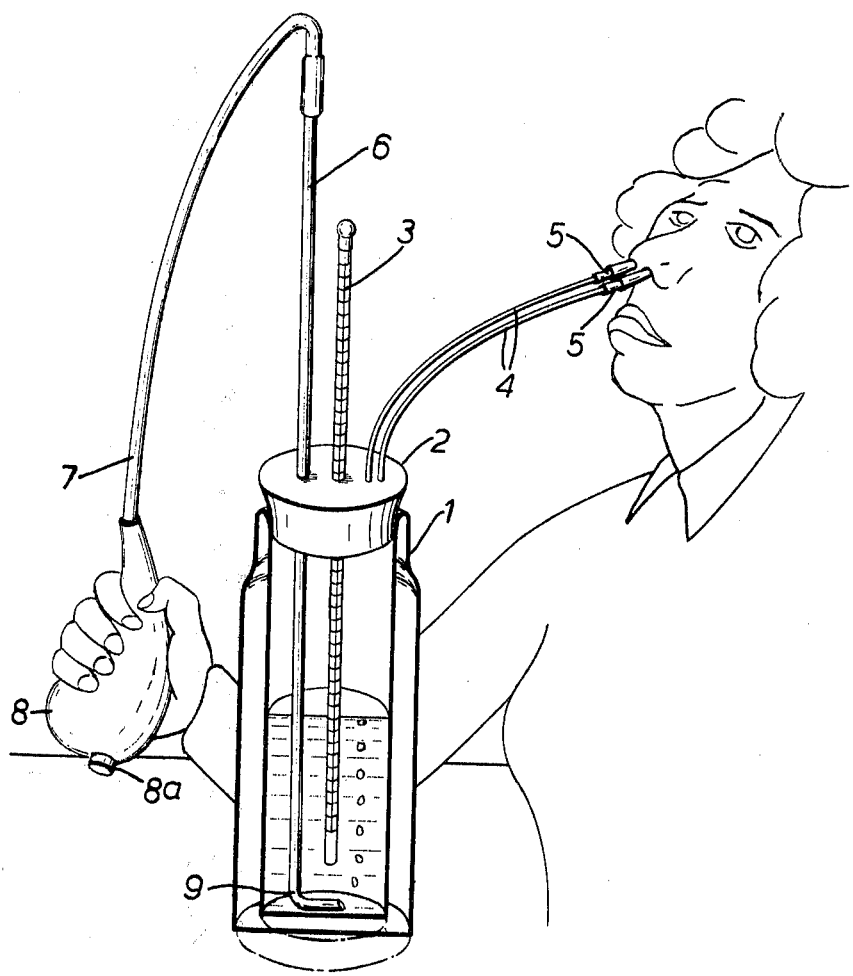
FIG. 1 is a generally schematic perspective view of first inhalation apparatus.

Referring now to FIG. 1, there is shown inhalation apparatus comprising an insulated container which is in the form of a vacuum flask 1 and which is closed at one end by means of a stopper 2. The stopper 2 is conveniently made of rubber and it serves as a closure means for the flask 1. Passing through the stopper 2 is a thermometer 3 which is arranged to measure the temperature of liquid contained in the flask 1. Air under pressure is fed to the flask 1 via a rigid tube 6 which passes through the stopper 2 and extends nearly to the bottom of the flask 1 so that air pumped through the tube 6 bubbles up through liquid contained within the flask 1 as shown.

Air which has been introduced into the flask 1 via the tube 6 and which has bubbled through liquid contained therein, is collected at the top of the flask 1 by means of inhalation tube means in the form of a pair of tubes 4. The tubes 4 pass through the stopper 2 at one end thereof and at their other end they are terminated in a pair of anatomically designed injector pieces 5. The tubes 4 may be made of rubber or a flexible plastics material. The injector pieces 5 are especially designed to fit closely into the nostrils so as to introduce directly the beneficial vapours which are pumped through the tubes 4. In order to provide air under pressure, the rigid tube 6 is fed via a flexible tube 7 from air supply means in the form of a hand pump 8. The hand pump 8 incorporates an inlet valve 8a and air can readily be pumped from the pump 8, via the tubes 6 and 7, into the flask. Although a manually operated pump 8 is shown in the drawing it will be appreciated that in alternative arrangements, the source of air may be an electric pump or a cylinder of compressed air.

In order to promote the production of a copious supply of air bubbles, the tube 6 at the end 9 remote the stopper 2 may be provided with a bubble generator (not shown) such as an air stone which, when fed with air under pressure, produces a large number of small bubbles.

In use of the inhalation apparatus it may be desirable to maintain the temperature of liquid placed in the container 1 at between 42° C. and 50° C. for the most beneficial effects to be afforded. The flask might conveniently hold one liter of warm water or water mixed with a prescribed medicament. It is apparent that the flask should be filled only about half full with liquid thereby to prevent penetration of liquid droplets into the tubes 4.

The stopper 2 may alternatively be made of any suitable material such as plastics or of natural cork. The injectors 5 which are fitted to the end of the tubes 4 are designed for comfortable penetration into the nostrils. The injectors 5 are also designed for removal from the tubes 4 so that the injectors 5 may be disinfected after use and, if desired, different types of injectors 5 may be fitted to the tubes 4. It is desirable that the tube 6 extends to the region of the bottom of the flask 1 so that air will pass through all layers of liquid in the flask 1. The tube 6 should ideally extend a minimum of 20 cm above the stopper 2 to prevent penetration of water into the tube 6 and the source of air supply, in the case when a hand pump is used for this purpose, so that liquid does not tend to find its way back along the tube 6 to the pump 8.

Figure 2:
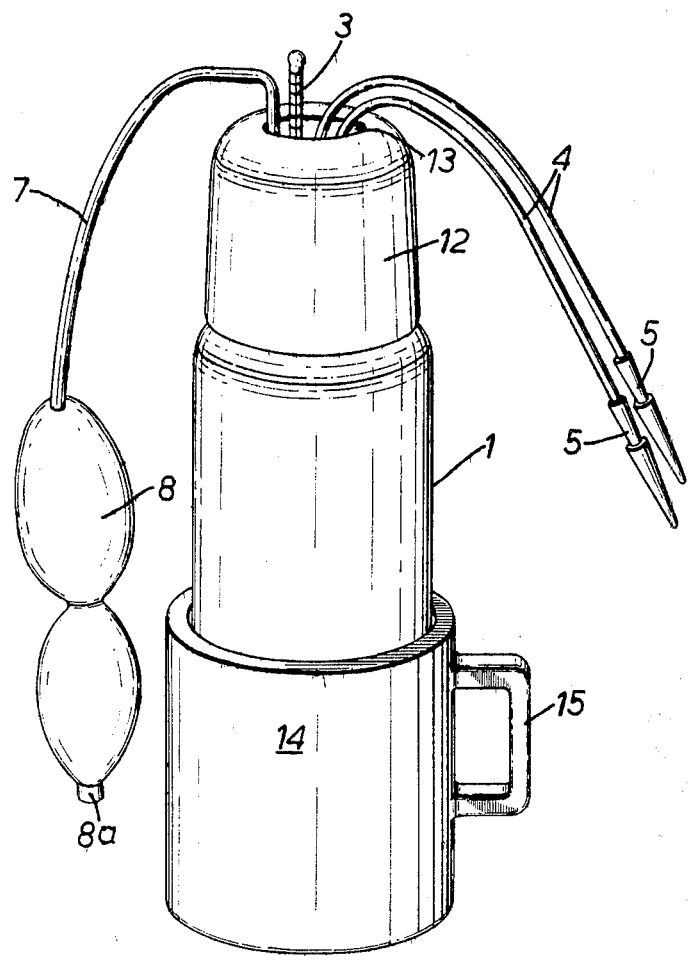
FIG. 2 is a perspective view of second inhalation apparatus.
Figure 3:
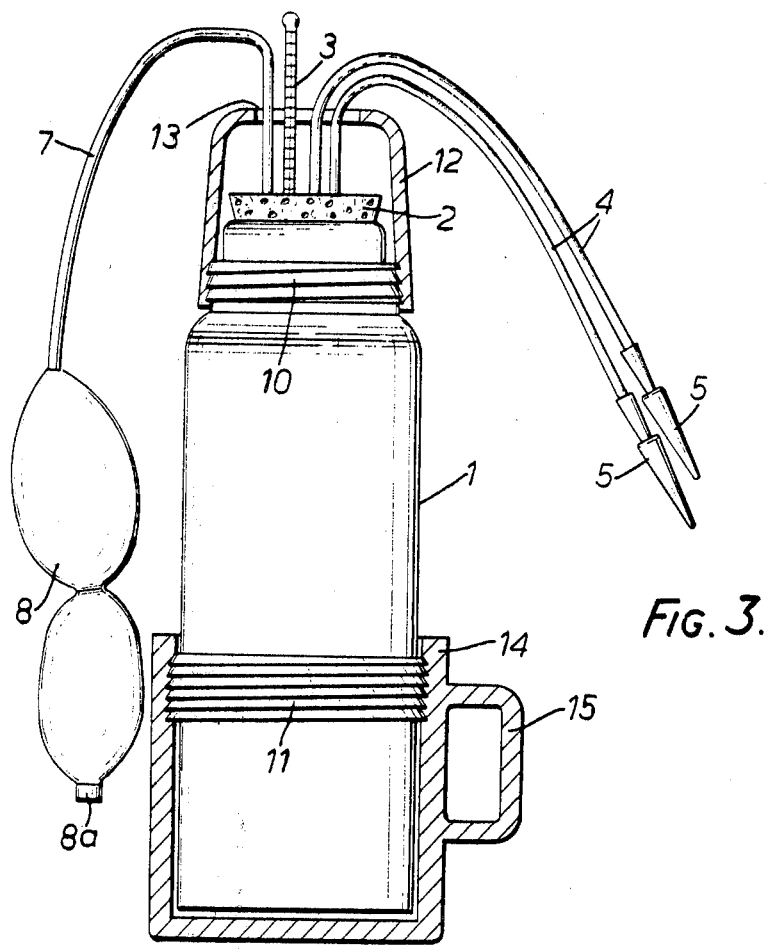
FIG. 3 shows the inhalation apparatus of FIG. 2 with various parts of the inhalation apparatus in section.

Referring now to FIGS. 2 and 3, similar parts as in FIG. 1 have been given the same reference numerals and their precise construction and operation will not again be given. In FIGS. 2 and 3, it can be seen that the flask 1 is provided with two threaded portions 10 and 11.

The threaded portion 10 allows a cover 12 to be screwed onto the flask 1. The cover 12 has an opening 13 which is smaller than the stopper 2. The opening 13 allows the tubes 4 and 7 and the thermometer 3 to pass through it, but not the stopper 2. Thus, if the flask 1 should inadvertently be over pressurised during use, for example if the air for the flask 1 is being provided from an electric pump or from a cylinder of compressed air, the pressure could cause the stopper 2 to blow out. The stopper 2 will not however cause any damage if it blows out because it will be constrained by the cover 12. The cover 12 will also be effective to stop a user of the inhalation apparatus getting splashed with the liquid in the flask 1 in the event that the stopper 2 should blow out.

The threaded portion 11 allows a cup 14 having a handle 15 to be screwed onto the flask 1. The cup 14 can be used for measuring the correct amount of warm water or other liquid for the flask 1. Thus, for example, the cup 14 can be employed to ensure that the flask 1 is not filled to more than half its volume in order to ensure that in the inhalation apparatus shown in FIGS. 2 and 3, water or other liquid does not penetrate up the tubes 4 and into the user's nostrils. If desired, the cup 14 can be provided with liquid volume measuring markings on its side.

Figure 4:
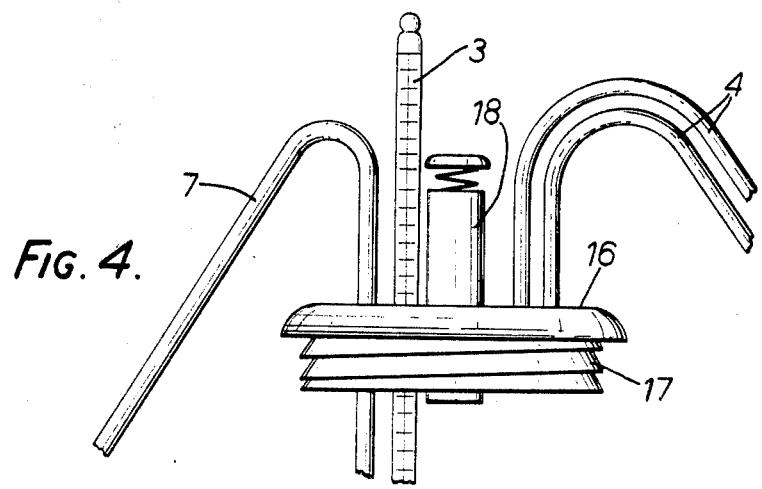
FIG. 4 shows part of third inhalation apparatus in enlarged detail.

Referring now to FIG. 4, there is shown the top part of inhalation apparatus having tubes 4 and 7 and a thermometer 3 as in FIGS. 2 and 3. In FIG. 4, the push in stopper 2 has been replaced by a screw in stopper 16 having a screw threaded portion 17 which screws directly into the flask 1. In case the flask 1 should inadvertently become over pressurised during use, the stopper 16 is provided with a safety valve 18 which will operate to release pressure from the flask 1 when the pressure in the flask 1 exceeds a predetermined value.

In operation of the inhalation apparatus described above it is advisable to disinfect and wash all parts before use. The flask 1 may then be filled with the prescribed medicament and/or warm water. The stopper 2 or 17 is firmly secured to the flask 1 and the injectors 5 are fitted to the tubes 4. The air supply is then started and after one to three minutes, during which time the temperature of the vapour can be tested, for example by touch, the injectors may be placed in the nostrils of a patient.

With inhalation apparatus according to the present invention, warm damp and medicated air may be injected directly into the respiratory tract of a patient and because air is fed under slight pressure to the patient little effort is required by the patient and indeed the process of breathing is actually assisted by utilising the inhalation apparatus. Also, it is possible to increase the concentration of medicament in the inhaled warm damp air without increasing the temperature to an undesirable level.

It is to be appreciated that the embodiments of the invention described above with reference to the drawings have been given by way of example only and that modifications may be effected. Thus, for example, the tube 6 or 7 could be provided with an obturator such as a ball valve obturator which is held in an open position away from a valve seat by a spring during normal operation of the inhalation apparatus. If the tube 6 or 7 should receive air at too great a pressure, then the air pressure will overcome the force of the spring and cause the ball valve obturator to sit on the valve seat, which will close the tube 6 or 7 and thus prevent the flask 1 from being over pressurised. A similar type of obturator, or other valve device if desired, may be employed in the inhalation tube means for stopping water being unintentionally forced up the inhalation tube means and into the user's nostrils. If desired, the inhalation tube means may initially be in the form of a single tube 4 which divides at any desired position along its length into two tubes for receiving the injectors 5. This single tube 4 may be provided with the ball valve obturator or other valve device.

I claim:

1. Apparatus for inhalation comprising a single vacuum flask for holding a liquid and from which liquid vapour is to be inhaled, closure means for closing one end of the flask after the liquid has been introduced, air supply means, a connecting tube which passes through the closure means and via which air for inhalation is arranged to be fed from the air supply means to a region inside the flask adjacent the end remote from the closure means so as to bubble up through the liquid when contained therein, inhalation tube means which passes through the closure means for collecting the air after it has bubbled up through the liquid and which is adapted at one end thereof remote from the flask to fit to the nostrils whereby direct inhalation of air and vapour into the nostrils is facilitated, a thermometer which passes through the closure means and which is for measuring the temperature of the liquid in the flask, and a measuring cup which is for measuring the amount of liquid to be provided in the flask and which screws over the bottom of the flask.

2. Apparatus according to claim 1 in which the inhalation tube means comprises two tubes, and in which the end of each of the two tubes remote from the closure means is fitted with an injector piece anatomically designed to fit the nostrils.

3. Apparatus according to claim 1 in which the connecting tube includes a length of rigid pipe which projects above the closure means and which passes through the closures means and extends into the container.

4. Apparatus according to claim 1 in which the air supply means comprises a manually operated pump.

5. Apparatus according to claim 4 in which the end of the connecting tube is terminated with an air stone gas bubble producer.

6. Apparatus according to claim 4 in which the closure means is a push in closure means, and including a safety cover for constraining the push in closure means in the event that the container should be over pressurised during use to the extent that the closure means is caused to blow out of the container.

7. Apparatus according to claim 4 in which the closure means is a screw closure means, and including a pressure release valve for releasing pressure from within the container in the event that the container should be over pressurized during use.

8. Apparatus according to claim 1 in which the closure means is a push in closure means, and including a safety cover for constraining the push in closure means in the event that the container should be over pressurised during use to the extent that the closure means is caused to blow out of the container.

9. Apparatus according to claim 1 in which the closure means is a screw closure means, and including a pressure release valve for releasing pressure from within the container in the event that the container should be over pressurised during use.

* * * * *